United States Patent [19]

Polak

[11] Patent Number: 5,114,421
[45] Date of Patent: May 19, 1992

[54] MEDICAMENT CONTAINER/DISPENSER ASSEMBLY

[76] Inventor: Robert B. Polak, 160 Kimberley Ave., Asheville, N.C. 28804

[21] Appl. No.: 400,370

[22] Filed: Aug. 30, 1989

Related U.S. Application Data

[63] Continuation-in-part of Ser. No. 910,407, Sep. 22, 1986, abandoned.

[51] Int. Cl.$^5$ .................................. A61M 31/00
[52] U.S. Cl. ............................ 604/403; 604/408; 604/410; 604/84
[58] Field of Search .............. 604/82, 83, 84, 85, 604/86, 87, 88, 92, 408, 409, 410, 415, 416, 414, 411

[56] References Cited

U.S. PATENT DOCUMENTS

| | | | |
|---|---|---|---|
| 3,881,640 | 5/1975 | Noble | 604/260 X |
| 4,356,012 | 10/1982 | Hofsetter | 604/324 X |
| 4,496,354 | 1/1985 | Steer et al. | 604/322 |
| 4,601,704 | 7/1986 | Larkin | 604/88 X |
| 4,609,369 | 9/1986 | Ball | 604/416 X |
| 4,661,100 | 4/1987 | Rechsteiner | 604/327 |
| 4,695,272 | 9/1987 | Berglund et al. | 604/84 |
| 4,798,605 | 1/1989 | Steiner et al. | 604/411 |
| 4,959,062 | 9/1990 | Gellman | 604/403 |
| 4,973,327 | 11/1990 | Goodrich et al. | 604/408 |

FOREIGN PATENT DOCUMENTS 2176096 12/1986 United Kingdom ............ 604/403

Primary Examiner—Robert A. Hafer
Assistant Examiner—Kerry Owens
Attorney, Agent, or Firm—Klauber & Jackson

[57] ABSTRACT

A disposable container/dispenser assembly for the extended storage and direct intravenous administration of a medicament includes a syringe barrel defining a main chamber for containing a liquid, the barrel including an upper opening in communication with the main chamber; an auxiliary barrel defining an auxiliary chamber for containing a drug to be mixed with the liquid, the auxiliary barrel including second and third spaced and opposing openings in communication with the auxiliary chamber; a first impermeable membrane for sealing the first opening of the main body; a second impermeable membrane for sealing the second opening of the auxiliary body; the first and second openings being in line with each other when the auxiliary body is connected with the main body; a third impermeable membrane secured to the auxiliary body for covering and sealing the third opening; and a plunger slidably positioned outside of the auxiliary body for rupturing the first through third membranes.

55 Claims, 9 Drawing Sheets

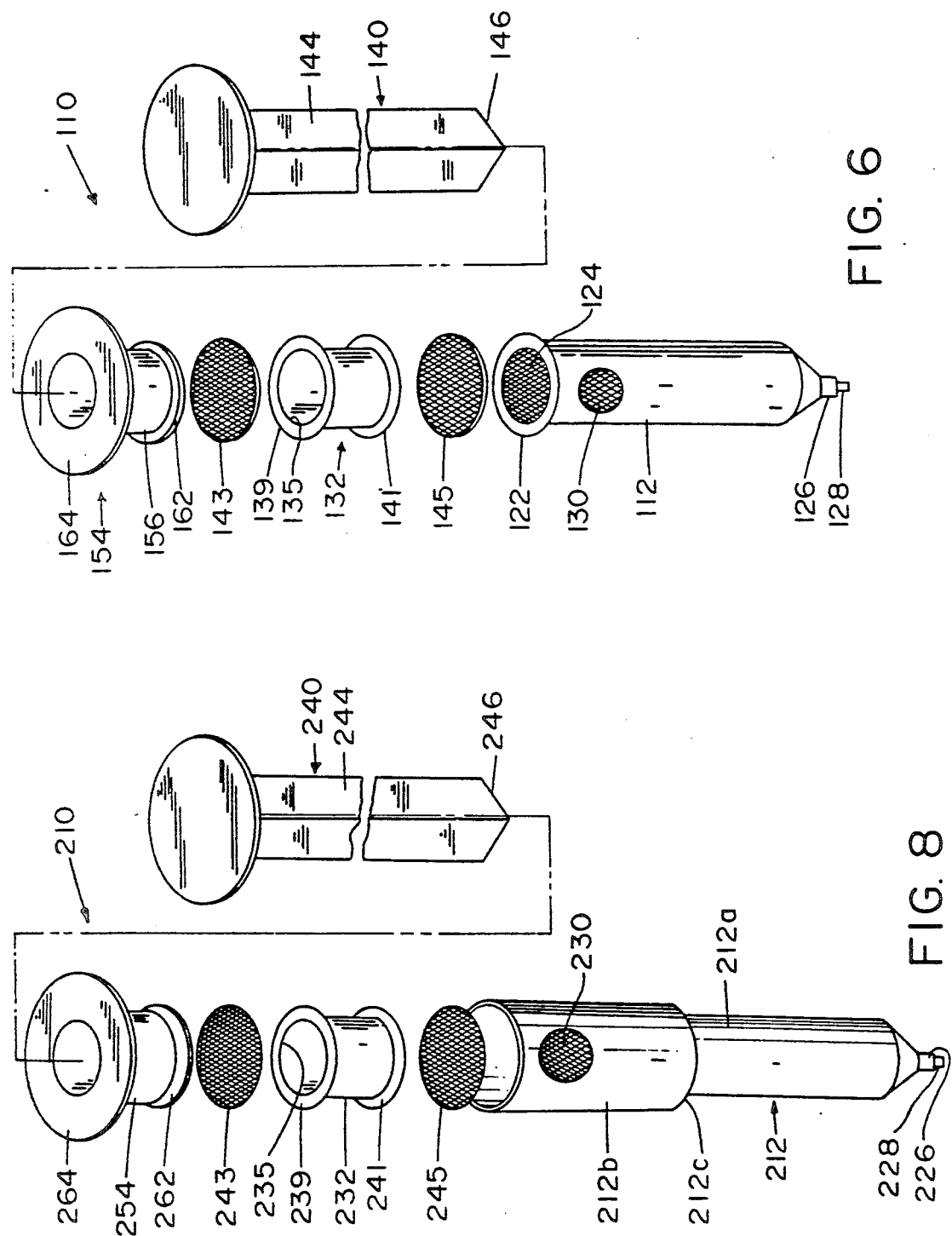

MEDICAMENT CONTAINER/DISPENSER ASSEMBLY

REFERENCE TO RELATED APPLICATION

The present Application is a Continuation-In-Part of copending application Ser. No. 910,407, filed Sept. 22, 1986, ABN. by the same inventor herein, and entitled MEDICAMENT CONTAINER/DISPENSER ASSEMBLY.

BACKGROUND OF THE INVENTION

This invention relates generally to medicament container/dispensers such as intravenous bags, bottles or the like, and more particularly, is directed to such devices as are prepared and used for the intravenous delivery of medicaments in premeasured dosages.

It is estimated that over 675 million intravenous (IV) containers are sold, and that about 240 million intravenous (IV) unit doses of various medicaments or drugs are given annually in the United States. In the past, most of these doses have been prepared under sterile conditions in hospital pharmacies. Recently, however, a number of pharmaceutical manufacturers have been producing and selling some of the more popular drugs in small pre-mixed IV bags, typically in sizes of 50 cc and 100 cc. Because of the overall labor savings, economy and ease of use, these products have gained in popularity, and sales thereof have increased dramatically.

However, although the IV bags are generally suitable for drugs which are stable at room temperature when premixed, unstable drugs cannot be contained in premixed form in such IV bags. To overcome this problem, some of these products are being packaged and sold in frozen form, or alternatively, in a double-bag configuration in which the contents of one IV bag can be released into the contents of the other IV bag to mix the components at a subsequent time. As will be appreciated, such double-bag configuration is relatively expensive and cumbersome to manufacture and use. In an alternate system, the IV bag is provided with a vial port for receiving a drug-containing vial which is screwed thereinto. This IV bag with a separately packaged drug vial is also relatively expensive and cumbersome to use.

In an attempt to cure the above problems, various devices have been provided. Specifically, various containers have been provided in which an unstable drug is separated from a stable drug by a rupturable membrane. In such case, a piercing or cutting element is provided for rupturing the membrane in order to mix the unstable drug with the liquid medicament.

For example, U.S. Pat. No. 2,721,552 to Nosik discloses a multiple chamber container in which, as shown in FIG. 5 thereof, a tubular shaped receptacle has an opening at the upper end thereof and a sterile liquid, such as water, is held within the receptacle. The upper end of the receptacle is sealed by a rupturable membrane. A second chamber is formed in an elastic deformable closure member that has a dependent flange in overlapping engagement with the upper end of the receptacle, so as to secure the closure member with the receptacle. A bore is provided in the closure member and has a tubular piercing member slidably retained therein. The lower end of the bore is sealed by a rupturable membrane. A solid medicament is positioned within the bore for mixing with the liquid in the receptacle. Specifically, the closure member is deformable so as to move the tubular piercing member downwardly so as to rupture the membrane closing the lower end of the bore of the closure member and the membrane closing the upper end of the receptacle. As a result, the solid medicament within the bore falls into and mixes with the liquid. The mixed material can then be removed with a hypodermic needle. In addition, the piercing member may be sealed to the closure member to prevent the escape thereof within the receptacle.

However, such arrangement has various disadvantages. In the first place, there is the possibility that accidental pressure on the closure member, during shipping or storage, will result in the piercing member rupturing the membranes, thus rendering the container, or at least the closure member portion thereof if separated from the container, unusable. As a result, shipping and storage of such container is relatively difficult and expensive. Further, because of the specific arrangement in which the piston is slidably positioned within the bore of the closure member, construction of the closure member becomes relatively complicated and expensive. Also, when compressing the closure member to rupture the membranes, there is an undesirable increase in pressure, or a back-pressure, provided in the receptacle. Accordingly, Nosik cannot be used as an IV container/dispenser, since without any means of pressure equalization, not only will there be a pressure build-up when the closure is ruptured, but also, as the liquid flows from the container, a vacuum will form which will slow and then stop the evacuation of the container.

In addition, in Nosik, the puncturing element is a tube which falls into the solution or is attached to the top of the container. Clearly, it is not desirable to have a free floating element in an IV container. On the other hand, if the puncturing or piercing tube is attached, when the sealing cap is depressed so as to force the piercing tube into its cutting relation, the piercing tube will block the opening which it has created unless the sealing cap springs back to its initial position, which cannot be assured. See also U.S. Pat. Nos. 2,275,567 to Smith; 3,840,136 to Lanfranconi et al; 3,968,872 to Cavazza; U.S. Pat. No. 4,187,893 to Bujan; 4,417,890 to Dennehey et al; 4,515,586; U.S. Pat. No. 4,601,704 to Larkin; and U.S. Pat. No. 4,693,711 to Bremer et al for similar disclosures. Also of interest in this regard are U.S. Pat. Nos. 3,306,563; 3,915,212; 4,161,178; 4,294,351; 4,392,850; 4,467,588; 4,548,606; 4,602,910; 4,608,043.

In addition, similar devices are known for use with syringes. For example, U.S. Pat. No. 4,693,706 to Ennis discloses a two compartment mixing syringe having an inner cylindrical barrel which is open at one end and closed at its opposite end by a thin membrane bonded thereto. The inner cylindrical barrel contains a diluent. A plunger is slidably inserted in the inner cylindrical barrel and has a sliding, sealing head which applies pressure to the diluent therein to rupture the membrane when the plunger is advanced. The inner barrel is slidably inserted in an open end of an outer barrel in sealing relationship therewith. The outer barrel contains a liquid or solid drug for mixing with the diluent in the inner cylindrical barrel when the membrane is ruptured. The mixture is discharged from the outer barrel via the tip thereof when the plunger is advanced axially in the inner barrel.

However, with this device, sealing of the diluent in the inner cylindrical barrel occurs by reason of the thin membrane bonded at the lower end thereof and the plunger at the opposite end thereof. Although the thin membrane is sufficient to provide an adequate seal for the diluent, the plunger may not be sufficient to provide an adequate seal for long-term storage. As a result, the diluent within the inner cylindrical barrel may deteriorate over time. Also, by its very nature, the two-barrel syringe requires close mechanical tolerances in order to function properly without any back-flow of the ingredients and with smooth mechanical operation. Thus, this device will be relatively expensive to manufacture. Still further, this device also poses the same problem as that discussed above with respect to the container of Nosik in that accidental pressure on the plunger may rupture the thin membrane secured to the lower end of the inner cylindrical barrel. Thus, shipping and storage of the mixing syringe of Ennis becomes difficult and expensive. Also, the problem of back pressure when starting to depress the plunger is a concern. In addition, since the membrane is ruptured by hydrostatic pressure of the liquid driven by the advancing plunger, there is no mechanical cutting head for fracturing the membrane in a precise manner, and the actual manner and time of rupture is never fully defined, and will vary from unit to unit.

Still further, because the drug in the outer cylindrical barrel is sealed by the inner cylindrical barrel extending therein, and the diluent in the inner cylindrical barrel is sealed by the plunger, the entire assembly of the inner cylindrical barrel, outer cylindrical barrel and plunger must be shipped in assembled form, thus increasing the cost. In addition, because the mixing syringe must be shipped and stored in assembled form, the number of different types of mixing syringes, that is, the number of different combinations of drugs in the outer cylindrical barrel and diluent in the inner cylindrical barrel is increased. A simple example of this increase in the number of combinations will suffice. Assume that there are three different types of drugs A, B, or C that can be held within the outer cylindrical barrel and three different types of diluent X, Y, or Z that can be held in the inner cylindrical barrel, there are nine possible combinations, namely, AX, AY, AZ, BX, BY, BZ, CX, CY, and CZ. However, there are only six different and separate elements, namely, A, B, C, X, Y, and Z. Therefore, if the inner cylindrical barrel and outer cylindrical barrel can be shipped and stored separately, there are only six types of containers that need be produced, that is, three inner cylindrical barrels and three outer cylindrical barrels, rather than the nine possible combinations. As the number of possibilities of drug mixing increases, the number of combinations also increases relative to the number of individual drugs that are used, thereby adding to the complexity of production and storage. For similar disclosures, see also U.S. Pat. Nos. 2,590,900 to Sommerstein; 3,255,752; 3,340,873 to Solowey; 3,380,451 to Porter et al; 3,685,514 to Cheney; 3,718,139 to Hanford; 3,838,689 to Cohn; 4,171,698 to Genese; 4,331,146 to Brignola; 4,405,317 to Case; 4,464,174 to Ennis; and 4,516,967 to Kopfer. Other devices which are less relevant by are related to the above are also found in U.S. Pat. Nos. 2,778,360; 3,447,432; 3,557,787; 3,636,950; 3,875,012; 4,048,999; 4,059,112; 4,089,432; 4,172,457; 4,289,648; 4,306,554; and 4,412,836.

Other patents which were uncovered or cited in the parent of the present Application are also noted for completeness as U.S. Pat. Nos. 2,854,977; 3,059,643; 3,128,917; 3,157,481; 3,193,993; 3,206,080; 3,881,640; 4,029,094; 4,356,012; 4,415,393; 4,432,760; 4,475,914; 4,583,971; 4,606,734; 4,614,515; 4,675,017; and 4,675,019.

Further, when IV solutions are administered to a patient, the IV container must be hung from a pole. It is highly desirable that the container hangs straight down so the medical personnel can easily determine the amount of solution that has been administered and the amount that remains in the container, by reading the graduations printed on the container. However, the hanger used with IV bottles and bags makes it difficult to hang the container in a perfectly straight position. Accordingly, incorrect readings may result, to the detriment of the patient. Further, with IV bags, when the bags are hung, the graduations may deform somewhat under the pull of gravity making the reading less than completely accurate.

OBJECTS AND SUMMARY OF THE INVENTION

Accordingly, it is an object of the present invention to provide a disposable container/dispenser assembly that avoids the aforementioned problems with the prior art.

It is another object of the present invention to provide a disposable container/dispenser assembly which is completely modular.

It is another object of the present invention to provide a disposable container/dispenser assembly in which two containers containing two different liquids and/or drugs can be stored separately and then assembled for use with a plunger which ruptures respective membranes of the containers, so as to mix the two components.

It is still another object of the present invention to provide such a disposable container/dispenser assembly in which the plunger is secured to the assembly during use thereof so as not to inadvertently rupture any membrane of the modular containers prior thereto.

It is yet another object of the present invention to provide a disposable container/dispenser assembly in which the number of types of components that need be manufactured and/or stored is reduced.

It is a further object of the present invention to provide a disposable container/dispenser assembly in which a main container thereof includes a liquid impervious, gas permeable membrane secured thereto for equalizing pressure therein.

It is a still further object of the present invention to provide a disposable container/dispenser assembly having extensions which insure that the assembly is hung from a pole in a substantially perfectly straight manner.

It is a yet further object of the present invention to provide an auxiliary body which contains a first material to be mixed with a second material in a main body, to which the auxiliary body can be attached, with the auxiliary body having a rupturable wall and a plunger for rupturing the same.

In accordance with an aspect of the invention, a disposable container/dispenser assembly for the extended storage and delivery of two incompatible materials, includes a main body defining a main chamber for containing a first one of the materials, the main body including an opening; an auxiliary body defining an auxiliary chamber for containing the second one of the materials to be mixed with the first material; at least one rupturable wall means positioned between the main body and the auxiliary body for preventing mixing of the materials; plunger means secured to an inner wall of the auxiliary body in opposing relation to the at least one rupturable wall means; and membrane means for permitting air to pass therethrough to the main chamber while preventing liquid from flowing therethrough from the main chamber, the membrane means being secured to the main body in covering and sealing relation to the opening of the main body, in a second area outside of the first area.

In accordance with another aspect of the invention, a disposable container/dispenser assembly for the extended storage and delivery of two incompatible materials, includes a main body defining a main chamber for containing a first one of the materials, the main body including a first opening in communication with the main chamber; an auxiliary body defining an auxiliary chamber for containing the second one of the materials to be mixed with the first material, the auxiliary body including second and third spaced and opposing openings in communication with the auxiliary chamber; first seal means for sealing the first opening of the main body with respect to the second opening of said auxiliary body, when the auxiliary body is connected with the main body such that the first and second openings are in line with each other; second seal means secured to the auxiliary body for covering and sealing the third opening; and plunger means slidably positioned outside of the auxiliary body for rupturing the first and second seal means.

In accordance with still another aspect of the present invention, a disposable container/dispenser assembly includes a main body defining a main chamber for containing a liquid, the main body including an opening; and a membrane secured to the main body in covering and sealing relation to the opening, the membrane including first and second extensions extending from opposite sides thereof, each extension including at least one aperture therein for receiving a support therethrough so as to hang the main body in a substantially straight manner from the support.

The above and other objects, features and advantages of the present invention will become readily apparent from the following detailed description thereof which is to be read in connection with the accompanying drawings.

BRIEF DESCRIPTION OF THE DRAWINGS

FIG. 6 is an exploded, perspective view of the disposable container/dispenser syringe assembly of FIG. 5;

FIG. 8 is an exploded, perspective view of the disposable container/dispenser syringe assembly of FIG. 7;

DETAILED DESCRIPTION OF THE PREFERRED EMBODIMENTS

Figure 1:
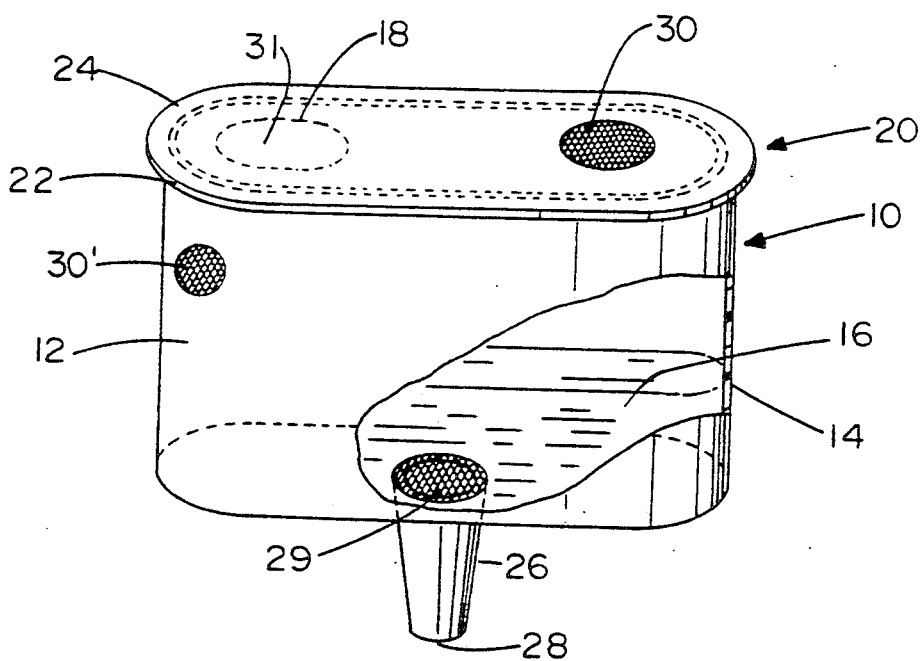
FIG. 1 is a perspective view of a main body of a disposable container/dispenser assembly according to a first embodiment of the present invention.

Referring to the drawings in detail, and initially to FIG. 1 thereof, a disposable container/dispenser assembly 10 according to a first embodiment of the present invention includes a substantially non-collapsible main body 12 defining a chamber 14 therein which contains a liquid 16, such as a diluent and/or adducts. As shown, main body 12 is formed in a configuration having a roughly ovoid cross section. However, the present invention is not limited by this configuration, whereby main body 12 can take any other suitable shape.

Preferably, main body 12 is a rigid plastic container made of a medical grade molded resin, such as polypropylene. The volume of main body 12 may range from 50 cc or less to 1,000 cc or more. The use of polypropylene is particularly advantageous herein as polypropylene may be heat sealed to itself and possess improved clarity and rigidity that is desired with IV containers.

An opening 18 is formed at the upper end 20 of main body 12, and an annular flange 22 surrounds opening 18 at upper end 20. In accordance with the present invention, an impermeable membrane 24 which does not permit liquid, vapor, or gas to pass therethrough is secured to annular flange 22 in covering and sealing relation to opening 18 by any suitable means, such as an adhesive, heat sealing, ultrasonic welding, or the like. Membrane 24 is sufficiently thin to permit rupturing thereof by a sharp object, as will be discussed in greater detail hereinafter. In this regard, impermeable, rupturable membrane 24 is preferably made from a three-layer, laminated film of polypropylene, aluminum, and polypropylene, although other combinations could be used. For example, impermeable membrane 24 could be constructed from two laminated layers of polypropylene and aluminum, from only aluminum, or other polymeric plastics and/or metal foils.

At the opposite lower end 26, main body 12 tapers down to a standard sized exit port 28 which can be manufactured with a rupturable closure incorporated therein or could be independently sealed with plastic or a similar composition. Sealed exit port 28 is rupturable in order to cause the liquid 16 to flow out of main body 12. With the present invention, rupture may be accomplished by any manner of providing an opening in exit port 28, such as puncturing, tearing, cutting or the like. Specifically, exit port 28 could be ruptured by the thrust therethrough of a spike from a standard IV set (not shown). Further, a segment of conforming plastic or rubber tubing may extend over lower end 26 past exit port 28, and over to the spike of the IV set to assure that leakage at such joint is minimized Further, a hole is cut in impermeable membrane 24 and then closed by a semi-permeable membrane 30. Semi-permeable membrane 30 is a liquid impervious, gas permeable membrane which provides equalization of pressure in main body 12 as liquid 16 is exhausted therefrom through exit port 28, that is, which permits sterile air to enter main body 12 to provide pressure equalization. Semi-permeable membrane 30 may be made of any suitable material and is preferably made of polypropylene, although semi-permeable membrane 30 can be made from other materials, such as polypropylene, nylon, polysulfone or the like having a pore size of, for example, 0.02 μm, 1 μm or the like. Semi-permeable membrane 30 can be attached to impermeable membrane 24 by any suitable means, such as heat sealing, ultrasonic sealing or with an adhesive such as polyurethane. In addition, semi-permeable membrane 30 can be provided with additional rigidity by means of a reenforcing support or mesh (not shown). A pull-away metal foil tab (not shown) could be secured over semi-permeable membrane 30 in order to prevent any transport of gas or vapor therethrough until use of container 10.

Although semi-permeable membrane 30 has been described with respect to impermeable membrane 24, it is only necessary that semi-permeable membrane 30 be provided in main body 12 at a location above the level of liquid 16 therein. Thus, for example, as shown in FIG. 1, a semi-permeable membrane 30' can be located in a sidewall of main body 12 at a level above liquid 16.

In some instances, it may not be possible to obtain sufficient air flow through semi-permeable membrane 30 or 30'. In such case, it is possible to increase the surface area of such semi-permeable membrane while limiting the size of the cover opening. This can be accomplished in various ways. For example, semi-permeable membrane 30 or 30' can be formed in the shape of a cylinder or cone from a membrane sheet stock and attached, for example, by heat sealing or the like, to rupturable membrane 24 or in a side wall of main body 12, with the free end or apex thereof being positioned within main body 12. Alternatively, membrane 30 or 30' may comprise hollow fibers which have a much greater surface area and therefore much greater air flow rates than comparable semi-permeable sheet material. Thus, it is possible to obtain the necessary liquid flow from main body 12 with a very small venting window by attaching a bundle of hollow fibers, such as CELGARD polypropylene microporous hollow fibers, to rupturable membrane 24 or the side wall of main body 12, with the hollow fiber bundle pointing down into main body 12. The ends of the fibers could be sealed shut or, alternatively, they could be bent upward through an arc and attached to an opening in another part of main body 12 or rupturable membrane 24.

In accordance with the first embodiment of the present invention, disposable container/dispenser assembly 10 further includes an auxiliary body 32 formed from a flexible, impermeable film such as polypropylene or other polymer plastic, or a multi-layer, laminated material, such as a laminated film of polypropylene and aluminum. It will be appreciated from the discussion hereinafter that the dimensions of auxiliary body 32 are less than those of main body 12 so that it can be secured on impermeable membrane 24 of main body 12. In this regard, auxiliary body 32 includes a rupturable base membrane 34 and a dome section 36 secured with base membrane 34 by any suitable means, such as heat sealing, adhesive or the like, so as to define a chamber 38 therein. An unstable drug, for example, a medicament 48, is positioned in chamber 38 prior to sealing dome section 36 with base membrane 34.

In addition, a piercing element 40 is secured to the inner wall of dome section 36 at the upper end thereof, by any suitable means, such as heat sealing, molding, ultrasonic welding, adhesive or the like. Piercing element 40 preferably includes a base 42 secured to dome section 36 and a cruciform shaped shaft 44 secured to base 42, shaft 44 having a free end with a cutting edge or elements 47 thereat. The cutting elements can be made of plastic as an integral part of shaft 44, or they can be attached to the end of shaft 44 by any suitable means, such as a medically approved adhesive, molding cutting elements 47 into the end of shaft 44, mechanical attachment or the like. Further, cutting elements 47 of piercing element 40 can be made of any suitable material, such as plastic or stainless steel, with base 42 and shaft 44 being made of polypropylene or the like.

Figure 2:
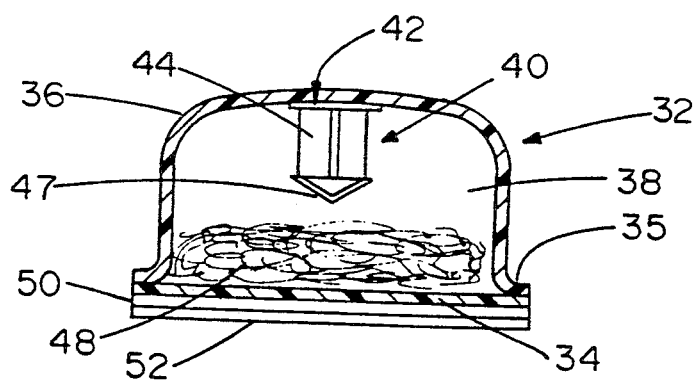
FIG. 2 is a cross-sectional view of an auxiliary body of the disposable container/dispenser assembly of the first embodiment of the present invention for use with the main body of FIG. 1.
Figure 2B:
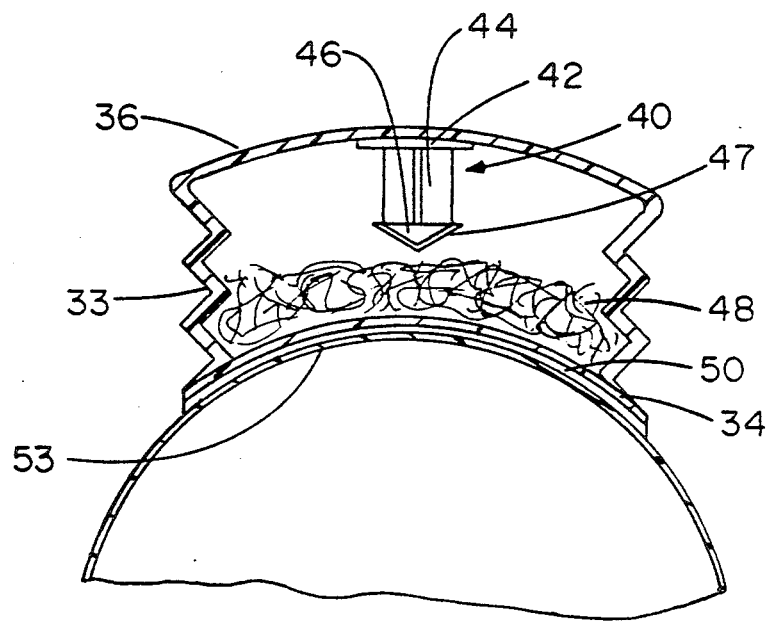
FIG. 2B is a cross-sectional view similar to FIG. 2 in which the walls are accordion pleated and the auxiliary body is attached to an IV bag.
Figure 2A:
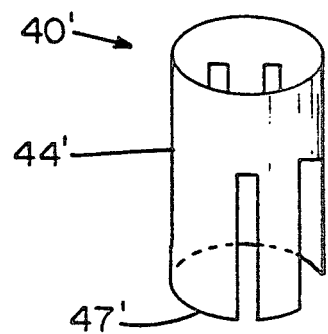
FIG. 2A is a perspective view of another piercing element according to the present invention.

Alternatively, a piercing element 40' in the form of a slotted tube 44' with sharp cutting edges 47' can be provided, as shown in FIG. 2A. When using such piercing elements 40 and 40', even when the hole in membrane 34 is cut and the piercing element remains in such cut hole, liquid can still travel between chambers 14 and 38, unlike the case of the solid piercing tube of Nosik.

It will be appreciated that auxiliary body 32 can be manufactured in any number of suitable ways. For example, auxiliary body 32 can be vacuum formed from a sheet of plastic such as polypropylene. In order to permit auxiliary body 32 to deform, it could be constructed in various configurations in addition to that shown in FIG. 2, for example, the walls thereof may be constructed with accordion pleats 33, as shown in FIG. 2B, it may be constructed with a hemispherical shape, or auxiliary body 32 could be manufactured so as to provide a stack of interconnected, progressively smaller, concentric cylinders. However, it has been found that a very simple dome-shaped body as shown in FIG. 2 is particularly effective. When forming auxiliary body 32, an annular flange 35 is formed at the open end of dome section 36, with base membrane 34 being secured thereto. In such case, a recess can be molded into the inner surface of dome section 36 at the upper end thereof and base 42 of piercing element 40 can be fit into such a recess with a mechanical friction fit, or by any other suitable means such as heat sealing, adhesive or the like.

Alternatively, auxiliary body 32 can be made by a blow molding method or by injection molding the same. When injection molding is used, piercing element 40 can be made as an integral part of molded auxiliary body 32. However, when using an injection molding method, a container with accordion pleated walls cannot be formed.

With the exception of vacuum forming, it is not possible to construct auxiliary body from an aluminum composite, although an aluminum film barrier could be formed by methods such as vapor deposition on the plastic, so as to provide total protection from moisture and gas transmission for auxiliary body 32. If it is not possible or practical to place a metal layer on the plastic, the auxiliary body could be packed in a vaporproof packaging material, such as a metal foil pouch which could be readily removed prior to using auxiliary body 32.

Auxiliary body 32 is sealed to impermeable membrane 24 in such a way that cutting elements 47 face impermeable membrane 24. It is important, however, that when attaching auxiliary body 32 to main body 12, semi-permeable membrane 30 is completely outside of the area covered and sealed by auxiliary body 32 in order to provide pressure equalization during use and to prevent water vapor from coming into contact with the water sensitive material in container 36. Auxiliary body 32 can be secured to impermeable membrane 24 by any suitable means, such as ultrasonic welding, heat sealing, a medically acceptable contact adhesive or the like.

Further, it will be appreciated that auxiliary body 32 can be formed with main body 12 in an initial manufacturing process. In such case, there is no need for two membranes 24 and 34, that is, a single membrane can be used.

In operation, in order to mix unstable medicament 48 with liquid 16, it is only necessary to press down on base 42 of piercing tube 40. As a result, cutting elements 47 rupture base membrane 34 and impermeable membrane 24 so that the medicament 48 falls into liquid 16. Auxiliary body 32 may then return to the original shape shown in FIG. 2, and liquid 16 and medicament 48 are then mixed by shaking assembly 10, making sure that liquid 16 enters all areas of auxiliary body 32, as well as main body 12.

Figure 3:
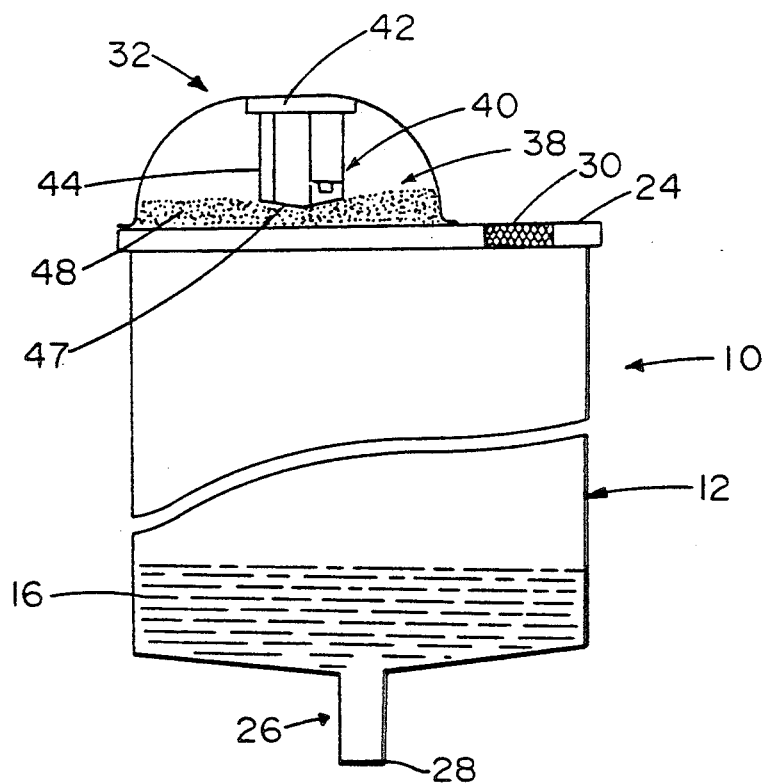
FIG. 3 is a cross-sectional view of the disposable container/dispenser assembly according to the first embodiment of the present invention in assembled condition.
Figure 4:
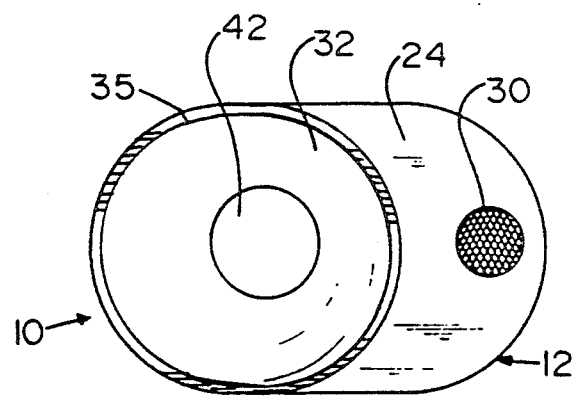
FIG. 4 is a top-plan view of the disposable container/dispenser assembly of FIG. 3.

In order to reduce inventory and/or storage costs, it is preferable that main body 12 and auxiliary body 32 be shipped and stored separately, and assembled just prior to use. Specifically, as shown in FIG. 2, the lower surface of base membrane 34 of auxiliary body 32 is preferably coated with a medically acceptable contact adhesive 50, with a pressure release backing 52 thereon. Therefore, it is only necessary to remove pressure release backing 52 and adhere auxiliary body 32 onto impermeable membrane 24, as shown in FIGS. 3 and 4. Pressure equalization is obtained by semi-permeable membrane 30, which is not affected by the operation of piercing tube 40 when medicament 48 is mixed with liquid 16. Accordingly, when medicament 48 mixes with liquid 16 and the contents thereof exit through exit port 28, semi-permeable membrane 30 ensures pressure equalization. Further, by providing auxiliary body 32 separately adherable to main body 12, it is readily easy to combine different types of medicament 48 with different types of liquid 16 at the time of use, thereby reducing the number of different types of items that need be stored and shipped.

It will be appreciated that, although auxiliary body 32 has been discussed for use with a substantially noncollapsible main body 12, auxiliary body 32 can be used with an IV bag 53, as shown in FIG. 2B. In such case, upon removal of pressure release backing 52, auxiliary body 32 can be secured to the outer surface of the IV bag. Since a greater physical force is required to penetrate the IV bag than is needed to penetrate impermeable membrane 24, more stress is introduced into the sealing areas and the ruptured edges may be ragged. In such case, it is desirable to utilize stainless steel cutting elements 47.

It will be appreciated that, with the aforementioned assembly 10, puncturing of membranes 24 and 34 may generate small particles from the plastic resin or foil. Thus, these particles would need to be filtered prior to or during administration of the solution. To overcome this problem, a standard filter can be placed in the IV line. Alternatively, a hydrophilic filter membrane 29 can be placed inside main body 12 just above exit port 28. Filter 29 can be attached to the bottom of main body 12 by any of the sealing methods discussed above, as well as by friction fitting the same into a recess formed in main body 12. Because of the potential for contamination, adhesive sealing is not particularly desirable. A suitable filter that can be used is a 5 μm filter sold under the trademark "Versipor" by Gelman Science, which is a hydrophilic membrane composed of an acrylic copolymer cast on a non-woven, nylon substrate.

Another consideration with assembly 10 is that of maintaining sterility thereof during handling when subsequently attaching auxiliary body 32 to main body 12. When auxiliary body 32 is attached directly to main body 12 at the factory, this problem does not exist. However, when attached at a later time shortly before use thereof, a peel-away, protective paper or plastic layer 31 is preferably secured on impermeable membrane 24 at the position where auxiliary body 32 is to be secured. In this manner, the lower surface of base membrane 34 is protected from contamination by pressure release backing 52, while the corresponding area on impermeable membrane 24 is protected by layer 31.

In addition, it may be necessary to provide a tamper evident feature with the present invention. This would provide an indication if membranes 24 or 34 are removed. The best approach is to use a sealing process which does not permit resealing. For example, membranes 24 and 34 can be secured to main body 12 and auxiliary body 32, respectively, by heat sealing, RF sealing, ultrasonically welding or the like, in which, once membranes 24 and 34 have been separated, they cannot be reconnected in any simple fashion. Although most pressure sensitive adhesives do not have this property, by providing an adhesive with a high tack strength and attaching it to relatively weak films, the same effect could be obtained. Thus, if membranes 24 and 34 are made of relatively weak films and are joined with a high tack adhesive, any attempt to separate the containers will result in destruction of one or both of the impermeable membranes 24 and/or 34.

As another alternative to providing a tamper evident container, a microencapsulated coloring material could be incorporated into the adhesive or other sealing layer of membranes 24 and 34 in a distinctive pattern, such as regularly spaced lines, that would appear when membranes 24 and 34 are sealed under pressure. This assumes, of course, that the material of membranes 24 and/or 34 is transparent. If the seal for membranes 24 and 34 is disturbed, and then resealed, a visible pattern would be clearly evident, and a different secondary pattern would be superimposed thereon.

Figure 5:
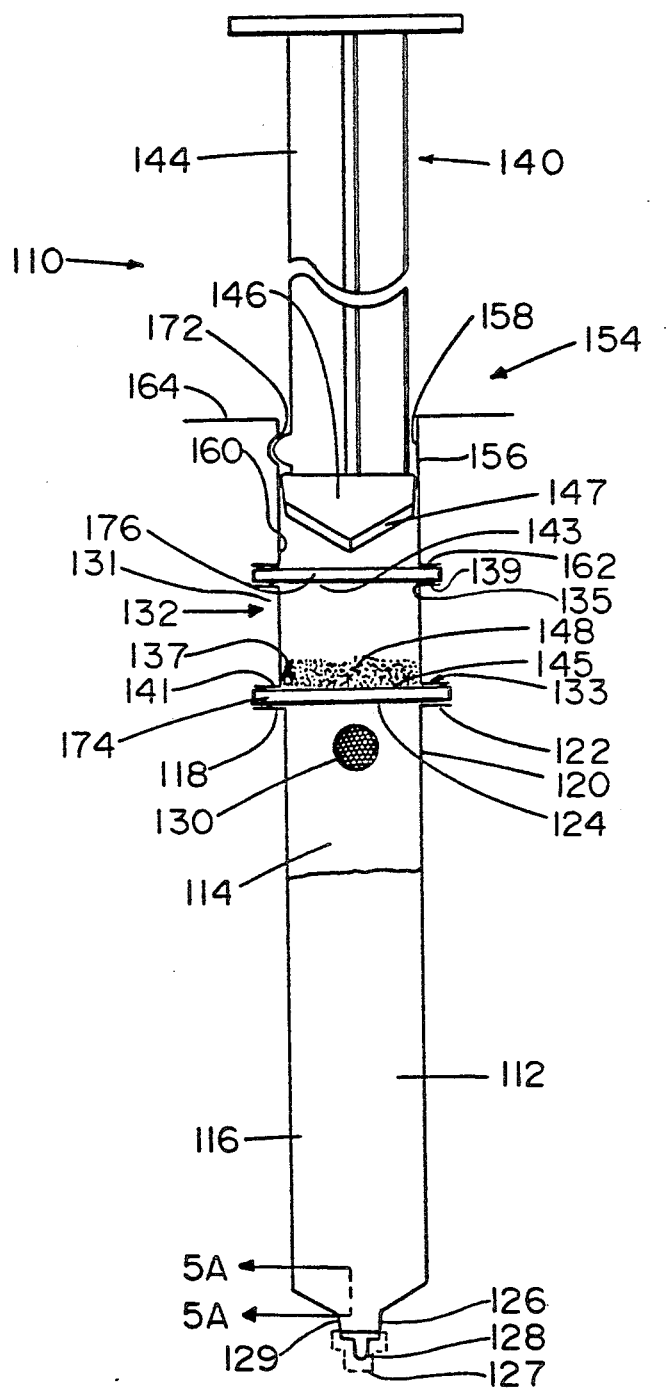
FIG. 5 is a cross-sectional view of a disposable container/dispenser syringe assembly according to a second embodiment of the present invention.

Referring now to FIGS. 5 and 6, a disposable container/dispenser syringe assembly 110 according to another embodiment of the present invention will now be described, in which elements corresponding to those identified in assembly 10 according to the first embodiments of FIGS. 1–4 are identified by the same reference numerals, augmented by 100, and a detailed description thereof will be omitted herein for the sake of brevity.

As shown therein, disposable container/dispenser assembly 110 includes a substantially non-collapsible main body 112 in the form of an outer syringe barrel defining a chamber 114 therein which contains a liquid 116 in the form of appropriate diluent and adducts. Preferably, main body 112 is a rigid plastic container made of a medical grade molding resin, such as polypropylene. An opening 118 is formed at the upper end 120 of barrel 112, and an annular flange 122 surrounds opening 118 at upper end 120.

At the opposite lower end 126, barrel 112 tapers down to a standard sized exit port 128 which can be manufactured with a rupturable closure incorporated therein or could be independently sealed with plastic or a similar composition. Sealed exit port 128 is rupturable in order to cause the liquid 116 to flow out of main body 112. With the present invention, rupture may be accomplished by any manner providing an opening in exit port 128, such as puncturing, tearing, cutting or the like. Alternatively, a hermetically fitted cap 127, as shown by dashed lines in FIG. 5, or similar device can be used to close and seal exit port 128. In addition, a liquid impervious, gas permeable membrane 130 can be formed in barrel 112 at a height above liquid 116 to provide pressure equalization.

The upper open end 120 of barrel 112 is sealed by an impermeable membrane 124 which is secured to flange 122 in covering and sealing relation to opening 118. Impermeable membrane 124 is preferably made of the same type of material as impermeable membrane 24 of assembly 10 of FIGS. 1-4, and thereby, can be punctured by a sharp instrument.

An auxiliary body 132 in the form of a barrel extension is also provided. Barrel extension 132 has a substantially cylindrical configuration which is open at opposite ends 131 and 133 thereof so as to form respective openings 135 and 137 thereat. An annular flange 139 surrounds opening 135 at upper end 131 thereof, and an annular flange 141 surrounds opening 137 at lower end 133 thereof. An impermeable membrane 143 is secured to annular flange 139 in covering and sealing relation to opening 135, and an impermeable membrane 145 is secured to annular flange 141 in covering and sealing relation to opening 137. Membranes 124, 143 and 145 can be secured to their respective flanges by any suitable means, such as heat sealing, ultrasonic welding, adhesives or the like. In accordance with the present invention, impermeable membrane 145 is first secured to flange 141, and then an unstable drug, such as medicament 148 is deposited in barrel extension 132. Thereafter, upper membrane 143 is sealed to annular flange 139.

A second barrel extension 154 is provided in the form of a cylinder 156 having an open upper end 158 and an open lower end 160, with an annular flange 162 surrounding the opening at lower end 160 and a large diameter annular flange 164 surrounding the opening at upper end 158. A plunger 140 is slidably received within cylinder 156 of second barrel extension 154, and includes a shaft 144, preferably of a cruciform shape. A natural rubber or elastomeric plunger head 146 having cutting elements 147 on the leading or free edge thereof, is secured to the lower end of shaft 144. Cutting elements 147 can be attached to plunger head 146 by any suitable means, such as medically approved adhesives, molding the cutting elements 147 into the end of plunger head 146, mechanical attachment or the like. Further, cutting elements 147, described above, can be made of any suitable material, such as plastic or stainless steel. Plunger head 146 maintains the seal with the inner wall of cylinder 156, and the inner walls of auxiliary body 132 and barrel 112. Plunger 140 can be releasably restrained within cylinder 156 by any suitable means, such as the detent assembly 172 shown in FIG. 5. In place of detent assembly, holes can be provided in alignment in cylinder 156 and shaft 144, and a plastic pin (not shown) removably secured therein.

It will be appreciated that membrane 130 is not essential in the syringe embodiments. This is because the plunger provides pressure equalization once the materials are mixed and the syringe is discharging. Thus, to the extent that pressure equalization is required at an early stage, a semi-permeable membrane can be used in barrel extensions 132 and 154.

In accordance with the present invention, barrel 112, first barrel extension 132 and second barrel extension 154 can each be packaged separately. Since second barrel extension 154 does not form part of second barrel extension 132, the possibility of rupturing impermeable membranes 143 and 145 during shipment and storage is prevented. It is also possible to package and ship the entire assembled device. As another alternative, it is possible to package barrel 112 as one unit, and extensions 132 and 154 as another unit.

In order to assemble the same just prior to use, flange 141 of second barrel extension 132 is secured on flange 122 of syringe barrel 112 by an adhesive 174 which, for example, can be provided on the lower surface of annular flange 141 with a pressure release backing (not shown) thereover, which is removed to expose the adhesive. In like manner, annular flange 162 of second barrel extension 154 is then secured with annular flange 139 of first barrel extension 132 by a similar adhesive 176, for example, on the lower surface of annular flange 162 and covered with a removable pressure release backing (not shown).

During use, it is only necessary to hold the assembly under flange 164 and depress plunger 140 such that cutting elements 147 rupture membranes 143, 145, and 124, so as to force medicament 148 into liquid 116 where it is mixed therewith. With this arrangement, the number of types of items that need be stored and shipped are reduced and the possibility of contamination and/or rupturing of the different membranes is reduced. Also, during depression of plunger 140, pressure equalization may be obtained through semi-permeable membrane 130.

Various types of materials and sealing methods can be used to construct syringe assembly 110. For example, barrel 112 and first barrel extension 132 can be made from polypropylene. Impermeable, rupturable membranes 143, 145, and 124, can be made from any suitable material, such as a three-layer laminated film of polypropylene, aluminum, and polypropylene, a two-layer film of polypropylene and aluminum, a single layer of aluminum foil or the like. Polymer plastics other than polypropylene could also be used.

It will be appreciated that, when driving plunger 140 through first barrel extension 132 and barrel 112, there would normally be a back pressure generated when the air in the syringe is compressed. Accordingly, as aforementioned, a semi-permeable membrane 130 may be provided in barrel 112 above the level of liquid 116 so as to provide pressure equalization and thereby relieve the back pressure, while maintaining a sterile environment in syringe assembly 110. In order to provide that no vapor or gas will enter semi-permeable membrane 130 before it is used, a pull-away metal foil tab (not shown) with an adhesive surface, could be attached over this area, such tab being removed prior to use of syringe assembly 110.

Although syringe assembly 110 has been described as a completely modular assembly, such syringe assembly 110 could be constructed in a totally assembled form or in only a partly modular system. For example, impermeable membrane 145 can be eliminated. In such case, annular flange 141 at open lower end 133 would be sealed directly on impermeable membrane 124. Thereafter, the unstable drug would be filled therein, and then impermeable membrane 143 would be secured to annular flange 139. Further, second barrel extension 156 could then be secured thereover, with plunger 140 being shipped separately, so as to prevent accidental rupturing of membranes 143 and 124. When the various modules 112, 132 and 154 are attached to each other during the initial manufacturing process, they can be joined by any suitable means such as heat sealing, ultrasonic welding, adhesive binding or the like. In this manner, a better seal can be achieved between the different elements, without the possibility of plunger 140 accidentally rupturing the membranes. However, plunger 140 can be shipped, assembled with the device, if it is fixed in place.

As with assembly 10, syringe assembly 110 can include a filter 129 at the lower end of syringe barrel 112 adjacent exist port 128 to prevent any particles resulting from the rupture of membranes 124, 143 and 145 from exiting through exit port 128.

Figure 5A:
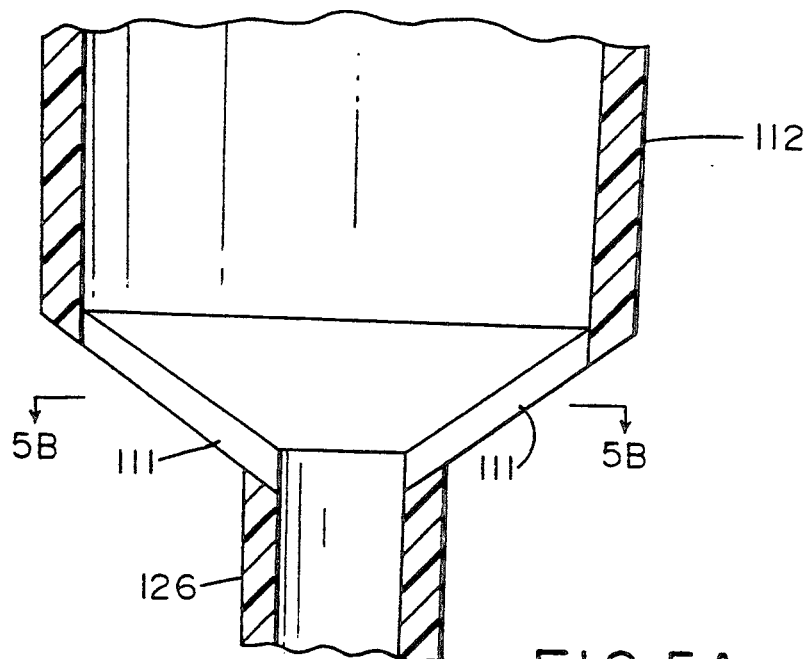
FIG. 5A is an enlarged cross-sectional view of a portion of the syringe assembly of FIG. 5, taken along line 5A—5B thereof.
Figure 5B:
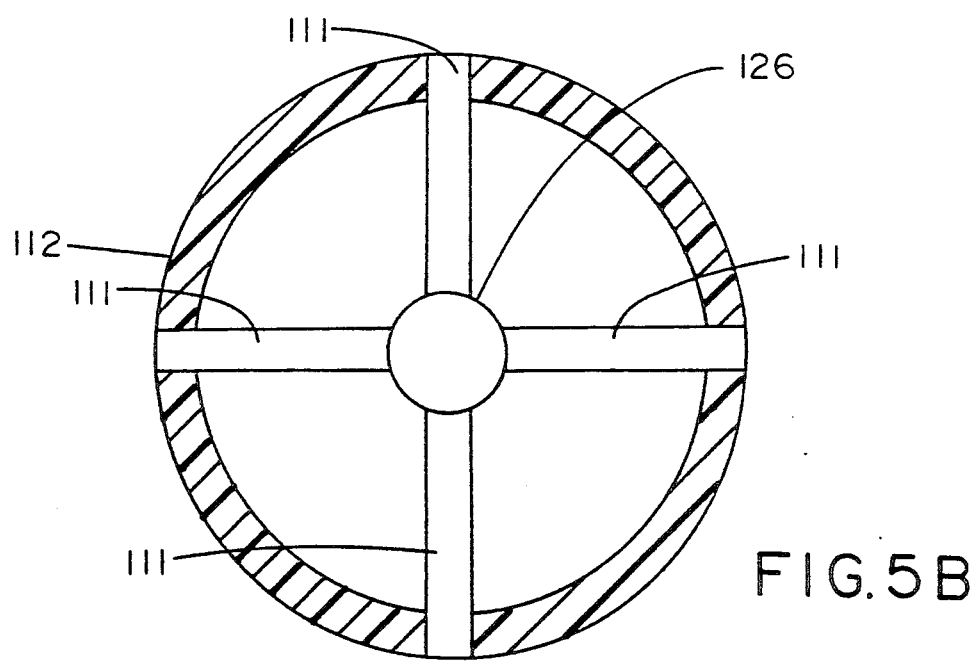
FIG. 5B is a cross-sectional view of the portion of the syringe assembly of FIG. 5A, taken along line 5B—5B thereof.

Further, since cutting elements 147 are positioned ahead of plunger head 146, cutting elements 147 will make contact with the bottom of syringe barrel 112 first, and thus, may prevent complete withdrawal of liquid 116 therefrom. Since the width of cutting elements 147 is small, this may not be a problem. However, on occasion, the removal of all liquid 116 may be necessary. In such case, syringe barrel 112 can be modified by providing it with slots or grooves 111 at the bottom thereof which can accommodate cutting elements 147, thus permitting the plunger head 146 of shaft 144 to cleanly hit the bottom of syringe barrel 112, as shown in FIGS. 5A and 5B. In order to ensure that cutting elements 147 are properly aligned so as to enter these slots, a positioning element can be placed at the upper end of syringe barrel 112 to make sure that the cutting elements and slots are properly positioned relative to each other.

In any event, it will be appreciated that syringe barrel 112, first barrel extension 132 and second barrel extension 154 are manufactured with close dimensional tolerances. As a result, the parts must be assembled with care in order to permit plunger 140 to advance through syringe assembly 110 without any problems. In order to facilitate such assembly, positioning guides (not shown) can be molded into the mating parts of syringe barrel 112, first barrel extension 132 and second barrel extension 154. For example, tongue and groove, or male and female joining guides, can be included in flanges 122, 139, 141 and 162, so that assembly 110 can be assembled readily with a minimum of trouble and expense.

Further, although the aforementioned syringe assembly 110 has been described with a semi-permeable membrane 130 incorporated into barrel extension 112 for providing pressure equalization, it is possible to provide such pressure equalization in other ways. For example, a small groove (not shown) can be cut, etched or molded along the length of the inside of barrel extensions 132 and 154. Such groove will tend to act as a pressure relief valve as plunger 140 travels through barrel extension 132 and before membrane 124 is ruptured.

Figure 7:
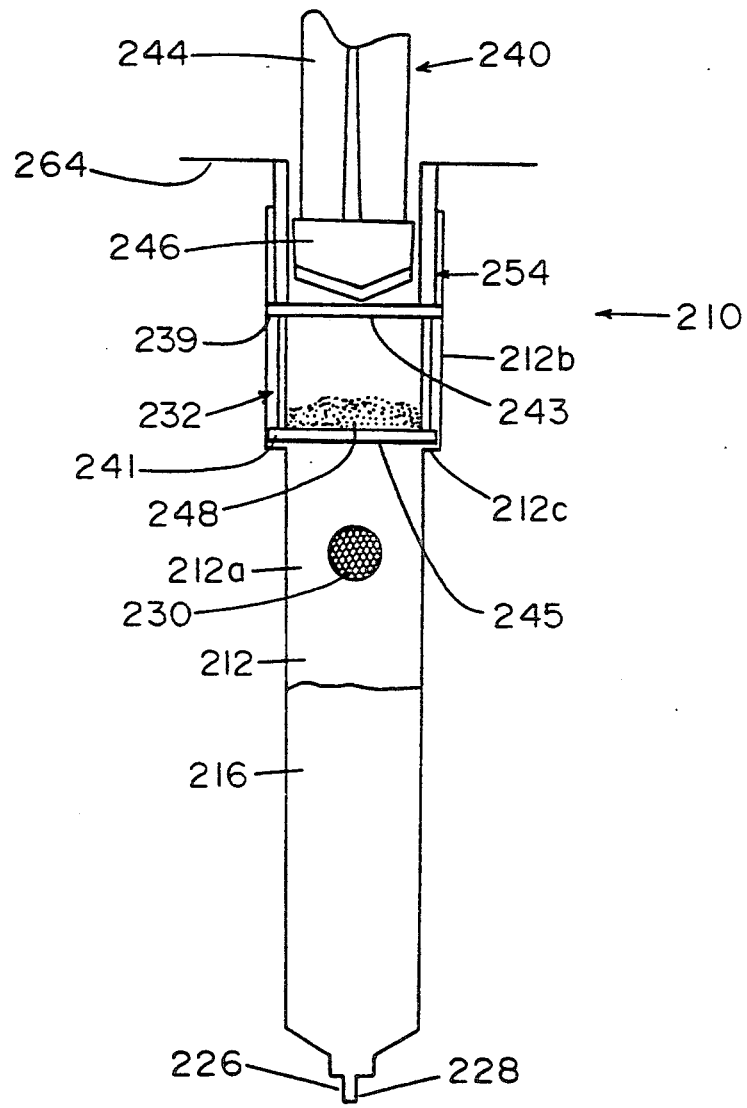
FIG. 7 is a cross-sectional view of a disposable container/dispenser syringe assembly according to another embodiment of the present invention.

Referring now to FIGS. 7 and 8, a disposable container/dispenser syringe assembly 210 according to another embodiment of the present invention will now be described in which elements corresponding to those described above with respect to disposable container/dispenser syringe assembly 110 of FIGS. 5 and 6 are identified by the same reference numerals, augmented by 100, and a detailed description thereof will be omitted herein for the sake of brevity.

Syringe assembly 210 differs from syringe assembly 110 in that syringe barrel 212 is formed with a lower section 212a of a first diameter and an upper section 212b connected therewith of a larger diameter, with sections 212a and 212b being in fluid communication. Accordingly, an annular shoulder 212c is formed between sections 212a and 212b. Liquid 216 is contained within lower section 212a. First barrel extension 232, second barrel extension 254 and plunger 240 are identical in utility to corresponding elements 132, 154, and 140 of syringe assembly 110 of FIG. 5. With this assembly, liquid 216 in barrel 212 is sealed by impermeable membrane 245 at the lower end of first barrel extension 232 which fits within upper section 212b with a friction sealing fit and rests on shoulder 212c. It should be noted that unstable drug 248 is contained within first barrel extension 232 between membranes 243 and 245. Second barrel extension 254 is fitted above first barrel extension 232 within larger diameter section 212b of syringe barrel 212. Plunger 240 can be shipped separately and inserted at a later time. Thus, the accidental rupturing of membranes 243 and 245 is prevented. However, plunger 240 could also be shipped with barrel extension 254 which could be connected to barrel 212 at a later time.

It will be appreciated that, with this arrangement, the dimensions are such that plunger 240 can travel freely through the length of first barrel extension 232 and syringe barrel 212.

It will be further appreciated that barrel extensions 232 and 254 can be fit within upper section 212b by any other suitable means. For example, barrel extensions 232 and 254 can be fit within upper section 212b with a friction fit, screw fit, luer-lock, or the like. In addition, an adhesive can be provided for adhering impermeable membrane 245 to shoulder 212c to prevent any possible leakage of powder or liquid once the membranes are ruptured. Further, this configuration could also include a filter membrane at the bottom of barrel 212 to prevent particles from exiting through the exit port, such filter membrane already described with respect to FIG. 5, and slotted grooves to contain the cutting elements, as already described with respect to FIGS. 5A and 5B.

Figure 9:
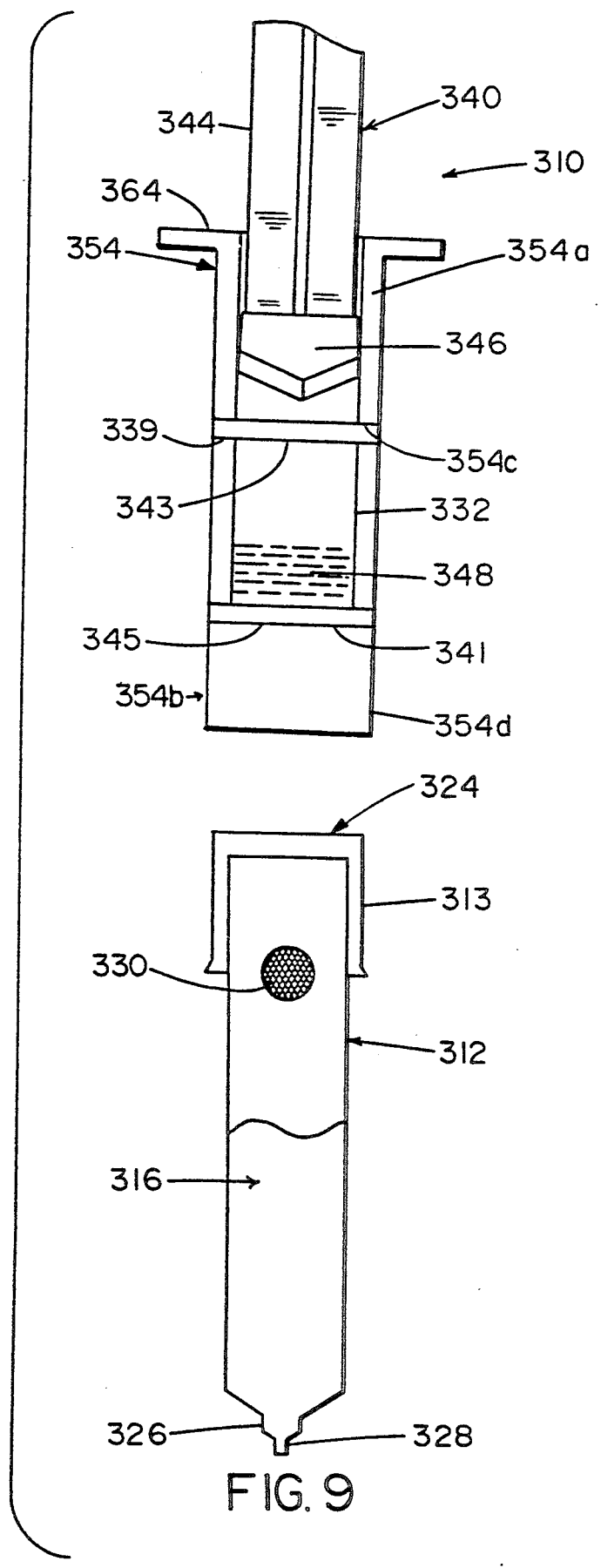
FIG. 9 is an exploded cross-sectional view of a disposable container/dispenser syringe assembly according to another embodiment of the present invention.

Referring now to FIG. 9, a disposable container/dispenser syringe assembly 310 according to another embodiment of the present invention will now be described in which elements corresponding to those described above with respect to disposable container/dispenser syringe assembly 210 of FIGS. 7 and 8 are identified by the same reference numerals, augmented by 100, and a detailed description thereof will be omitted herein for the sake of brevity.

With syringe assembly 310, second barrel extension 354 is provided with an upper section 354a of a first inner diameter and a lower section 354b connected therewith of a larger inner diameter but with the same outer diameter, and with sections 354a and 354b being in fluid communication. Accordingly, an annular shoulder 354c is formed between section 354a and 354b. First barrel extension 332 is fit within lower section 354b until impermeable membrane 343 abuts against shoulder 354c. An adhesive with a pressure release backing (not shown) can be provided over impermeable membrane 343. Thus, once the pressure release backing is removed, the adhesive is used to secure impermeable membrane 343, and thereby flange 339, to shoulder 354c.

It will be appreciated that, as shown in FIG. 9, the length of lower section 354b is greater than that of first extension 332 so as to provide an open portion 354d as part of lower section 354b. The opening thereat may be covered by a pull-away tab (not shown) to maintain sterility until barrel 312 and second extension 354 are mated.

Syringe barrel 312 has a thicker sealing section 313 around the upper end thereof which tightly fits within open portion 354d. The upper open end of syringe barrel 312 is covered in sealing relation with an impermeable membrane 324 having an adhesive and pressure release backing (not shown) thereon. When the pressure release backing is removed, syringe barrel 312 is inserted through open portion 354d and adhered to impermeable membrane 345 along annular flange 341. In effect, the arrangement of FIG. 9 is the converse of that shown in FIGS. 7 and 8. Alternatively, in place of thicker sealing section 313, syringe barrel 312 can have a diameter which provides a good sealing fit with the inner wall of open portion 354d. As already noted above with respect to FIGS. 5, 5A and 5B, the syringe may contain, at the bottom of barrel 312, a filter membrane and slotted grooves to contain the cutting elements.

Further, although the embodiments have shown different ways of connecting the different bodies, it will be appreciated that there are other different modes of connection which are too numerous to mention, but which are nevertheless covered by the present invention.

As discussed above, when IV solutions are administered to a patient, the IV container must be hung from a pole. It is highly desirable that the container hangs straight down so that the medical personnel can easily determine the amount the solution has been administered and the amount that remains in the container by reading the graduations printed on the container. However, the hanger used with IV bottles and bags makes it difficult to hang the container in a perfectly straight position.

Figure 10:
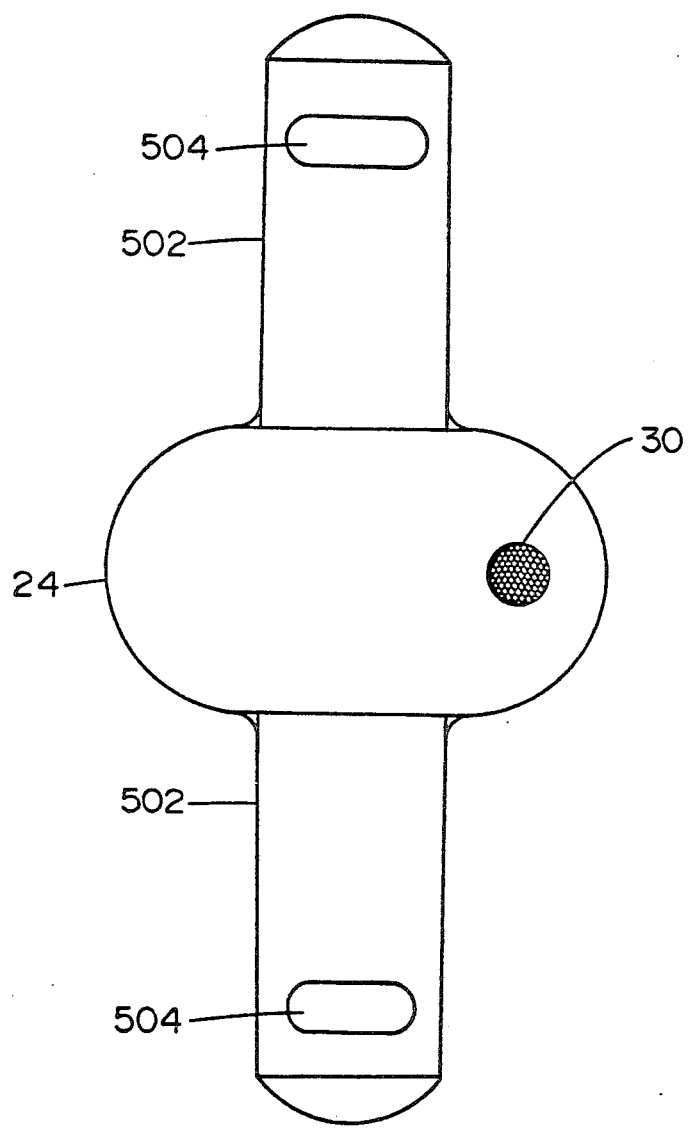
FIG. 10 is a plan view showing a support means useful for supporting the disposable container of FIG. 1.

Accordingly, as shown in FIG. 10, impermeable membrane 24 used with disposable container/dispenser assembly 10, includes extensions 502 at opposite sides thereof. Holes or slots 504 are placed in each extension 502 at the free end thereof and at equal distances from membrane 24. Accordingly, extensions 502 can be bent upwardly with slots 504 receiving a pole extension (not shown).

It will be appreciated that, while the present invention has been discussed with respect to unstable drugs, it could be used with any incompatible materials which cannot be stored together.

Having described specific preferred embodiments of the invention with reference to the accompanying drawings, it will be appreciated that the present invention is not limited to those precise embodiments, and that various changes and modifications can be effected therein by one of ordinary skill in the art without departing from the spirit or scope of the invention as defined by the appended claims.

What is claimed is:

1. A disposable container/dispenser assembly for the extended storage and delivery of two incompatible materials, comprising:
   a main body defining a main chamber for containing a first one of said materials, said main body including a main opening and a pressure equalization opening;
   an auxiliary body formed from a single, unitary deformable container section defining an auxiliary chamber for containing the second one of said materials to be mixed with said first material, said auxiliary body having an open end in facing relation to said main opening;
   at least one gas and vapor impermeable, rupturable wall means, positioned between the main body and the auxiliary body and secured to at least one of said main body and said auxiliary body for preventing mixing of said materials and for providing a gas and vapor barrier between materials in the main body and auxiliary body;
   plunger means fixedly secured to an inner wall of said container section in opposing relation to said at least one rupturable wall means; and
   membrane means for permitting air to pass therethrough to said main chamber while preventing liquid from flowing therethrough from said main chamber, said membrane being secured to said main body in covering and sealing relation to said pressure equalization opening of said main body, in a second area outside of said first area.

2. An assembly according to claim 1, wherein said main body is a rigid container made from a medical grade molded resin.

3. An assembly according to claim 2, wherein said medical grade molded resin is polypropylene.

4. An assembly according to claim 1, wherein said main body is an IV bag.

5. An assembly according to claim 1, wherein said main body includes a lower portion having an exit port thereat for removal of said first material.

6. An assembly according to claim 5, wherein said exit port is rupturable.

7. An assembly according to claim 5, further including filter means secured in said main body in covering relation to said exit port for preventing contaminant material from exiting through said exit port.

8. An assembly according to claim 1, wherein said at least one rupturable wall means includes an impermeable membrane in covering and sealing relation to said means opening.

9. An assembly according to claim 8, wherein said pressure equalization opening of said main body is formed in said impermeable membrane.

10. An assembly according to claim 8, wherein said pressure equalization opening is formed in a wall of said main body other than said at least one rupturable wall means.

11. An assembly according to claim 1, wherein said auxiliary body has a dome-shaped configuration.

12. An assembly according to claim 1, wherein said auxiliary body has accordion pleated walls.

13. An assembly according to claim 1, wherein said auxiliary body includes a deformable dome section and a rupturable base membrane secured to said dome section so as to define said auxiliary chamber.

14. An assembly according to claim 13, wherein said plunger means is secured to an inner wall of said dome section and has a free cutting edge facing said rupturable base membrane.

15. An assembly according to claim 13, wherein said auxiliary body further includes an adhesive coating on an outer surface of said base membrane and a pressure release backing thereover.

16. An assembly according to claim 1, wherein said plunger means includes a cruciform shaped shaft having cutting elements on a free end thereof.

17. An assembly according to claim 16, wherein said cutting elements are formed from one of stainless steel and plastic.

18. An assembly according to claim 1, wherein said plunger means includes a slotted tube having a free cutting edge.

19. A disposable container/dispenser assembly for the extended storage and delivery of two incompatible materials, comprising:
 a main body defining a main chamber for containing a first one of said materials, said main body including a first opening in communication with said main chamber;
 an auxiliary body defining an auxiliary chamber for containing the second one of said materials to be mixed with said first material, said auxiliary body including second and third spaced and opposing openings in communication with said auxiliary chamber;
 first seal means for sealing said first opening of said main body with respect to said second opening of said auxiliary body, when said auxiliary body is connected with said main body such that said first and second openings are in line with each other;
 second seal means secured to said auxiliary body for covering and sealing said third opening; and
 plunger means slidably positioned outside of said auxiliary body for rupturing said first and second seal means.

20. An assembly according to claim 19, wherein said main body is in the shape of a syringe barrel and includes an exit port.

21. An assembly according to claim 20, wherein said exit port is rupturable.

22. An assembly according to claim 20, further including a cap removably secured to said exit port.

23. An assembly according to claim 19, further including filter means secured in said main body in covering relation to said exit port for preventing contaminant material from exiting through said exit port.

24. An assembly according to claim 19, wherein said first seal means includes an impermeable membrane in covering and sealing relation to said first opening of said main body.

25. An assembly according to claim 19, wherein said auxiliary body has a substantially cylindrical configuration with opposite open ends having said second and third openings, respectively.

26. An assembly according to claim 19, wherein said first seal means includes an impermeable membrane in covering and sealing relation to said second opening of said auxiliary body.

27. A disposable container/dispenser assembly for the extended storage and delivery of two incompatible materials, comprising:
 a main body defining a main chamber for containing a first one of said materials, said main body including a first opening in communication with said main chamber;
 an auxiliary body defining an auxiliary chamber for containing the second one of said materials to be mixed with said first material, said auxiliary body including second and third spaced and opposing openings in communication with said auxiliary chamber;
 first seal means for sealing said first opening of said main body with respect to said second opening of said auxiliary body, when said auxiliary body is connected with said main body such that said first and second openings are in line with each other;
 second seal means secured to said auxiliary body for covering and sealing said third opening; and
 plunger means slidably positioned outside of said auxiliary body for rupturing said first and second seal means, said plunger means including a second auxiliary body defining a cylinder chamber and a plunger slidably positioned in said cylinder chamber, said second auxiliary body being securable with said first-mentioned auxiliary body.

28. An assembly according to claim 27, wherein at least one of said main body, said first-mentioned auxiliary body and said second auxiliary body further includes membrane means for permitting air to pass therethrough to said main chamber while preventing liquid from flowing therethrough from said main chamber.

29. An assembly according to claim 27, wherein said plunger includes a plunger shaft, a plunger head secured to a free end of said plunger shaft in slidably sealing relation with said second auxiliary body, and cutting elements on said plunger head for rupturing said first and second seal means.

30. An assembly according to claim 29, wherein said cutting elements are made from one of stainless steel and plastic.

31. An assembly according to claim 30, wherein said cutting elements are arranged in a cruciform shape.

32. An assembly according to claim 29, wherein said main body is in the shape of a syringe barrel and includes an exit port and slots at a lower end thereof adjacent said exit port for receiving said cutting elements.

33. An assembly according to claim 19, wherein said main body includes a first flange in surrounding relation to said first opening, said auxiliary body includes a second flange in surrounding relation to said second opening, and further including securing means for securing said first and second flanges together such that said first seal means and second seal means are in line.

34. An assembly according to claim 19, wherein said main body includes a first section defining said main chamber and a second section having a diameter greater than that of said first section and in fluid communication with said main chamber, said second section including a first opening in communication with said main chamber, and said auxiliary body is fit within said second section.

35. An assembly according to claim 34, wherein said main body includes an annular shoulder between said first and second sections, and said auxiliary body is positioned on said annular shoulder.

36. An assembly according to claim 35, wherein said first seal means is secured to said auxiliary body in covering and sealing relation to said second opening.

37. An assembly according to claim 35, wherein said plunger means is slidably positioned within said second section above said auxiliary body therein.

38. A disposable container/dispenser assembly for the extended storage and delivery of two incompatible materials, comprising:
- a main body defining a main chamber for containing a first one of said materials, said main body including a first section defining said main chamber, a second section having a diameter greater than that of said first section and in fluid communication with said main chamber, said second section including a first opening in communication with said main chamber, said annular shoulder between said first and second sections;
- an auxiliary body defining an auxiliary chamber for containing the second one of said materials to be mixed with said first material, said auxiliary body including second and third spaced and opposing openings in communication with said auxiliary chamber, said auxiliary body being fit within said second section and positioned on said annular shoulder;
- first seal means for sealing said first opening of said main body with respect to said second opening of said auxiliary body, when said auxiliary body is connected with said main body such that said first and second openings are in line with each other;
- second seal means secured to said auxiliary body for covering and sealing said third opening; and
- plunger means slidably positioned within said second section above and outside said auxiliary body for rupturing said first and second seal means, said plunger means including a second auxiliary body fit within said second section and a plunger slidably positioned inside said second auxiliary body.

39. A disposable container/dispenser assembly for the extended storage and delivery of two incompatible materials, comprising;
- a main body defining a main chamber for containing a fist one of said materials, said main body including a first opening in communication with said main chamber;
- an auxiliary body defining an auxiliary chamber for containing the second one of said materials to be mixed with said first material, said auxiliary body including second and third spaced and opposing openings in communication with said auxiliary chamber;
- first seal means for sealing said first opening of said main body with respect to said second opening of said auxiliary body, when said auxiliary body is connected with said main body such that said first and second openings are in line with each other;
- second seal means secured to said auxiliary body for covering and sealing said third opening; and
- plunger means slidably positioned outside of said auxiliary body for rupturing said first and second seal means, said plunger means including a cylinder and a plunger slidably positioned inside said cylinder and having cutting elements thereon for rupturing said first and second seal means, said cylinder including a first section having a first inner diameter and a second section connected with said first section and in fluid communication therewith, said second section having a second inner diameter greater than said first inner diameter so as to define an annular shoulder with said first section.

40. An assembly according to claim 39, wherein said auxiliary body is positioned within said second section of said cylinder in substantial abutment with said annular shoulder, said auxiliary body having a length which is less than that of said second section so as to define an open portion of said second section for receiving said main body.

41. An assembly according to claim 39, wherein said first seal means is secured to said auxiliary body in covering and sealing relation to said second opening.

42. A disposable container/dispenser assembly comprising:
- a main body defining a main chamber for containing a liquid, said main body including an opening; and
- a membrane secured to said main body in covering and sealing relation to said opening, said membrane including first and second extensions extending from opposite sides thereof, each extension including at least one aperture therein for receiving a support therethrough so as to hang said main body in a substantially straight manner from the support.

43. An assembly according to claim 42, wherein said main body is at least a semi-rigid container.

44. An auxiliary body for use with a main body defining a main chamber which contains a first material, said auxiliary body comprising:
- a single, unitary deformable container section which defines an auxiliary chamber for containing a second material to be mixed with said first material, said container section having an opening;
- gas and vapor impermeable, rupturable wall means secured to said container section for sealing said opening and for providing a gas vapor barrier;
- plunger means for rupturing said rupturable wall means, said plunger means positioned in said auxiliary chamber and fixedly secured to said container section in opposing relation to said rupturable wall means, said plunger means including means for preventing plugging of a hole ruptured in said rupturable wall means by said plunger means; and
- securement means for securing said rupturable wall means to an outer surface of a wall of said main body.

45. An auxiliary body according to claim 44, wherein said rupturable wall means has an area greater than a rupturing area of said plunger means.

46. An auxiliary body according to claim 44, wherein said securement means includes adhesive means for securing said rupturable wall means in substantially full contact with said outer surface of said wall of said main body.

47. An auxiliary body according to claim 44, wherein said rupturable wall means is substantially planar.

48. An auxiliary body according to claim 44, wherein said rupturable wall means has an arcuate configuration.

49. An auxiliary body according to claim 44, wherein said plunger means includes a cruciform shaped shaft having cutting elements on a free end thereof.

50. An auxiliary body according to claim 49, wherein said cutting elements are formed from one of stainless steel and plastic.

51. An auxiliary body according to claim 44, wherein said plunger means includes a slotted tube having a free cutting edge.

52. An auxiliary body according to claim 44, wherein said at least one deformable side wall has a substantially dome-shaped configuration.

53. An auxiliary body according to claim 44, wherein said at least one deformable side wall has accordion pleated walls.

54. An assembly according to claim 1, wherein said plunger means includes means for preventing plugging of a hole ruptured in said at least one rupturable wall means by said plunger means.

55. An assembly according to claim 1, wherein said at least one rupturable wall means includes a first rupturable wall secured to said main body in sealing relation to said main opening and a second rupturable wall secured to said auxiliary body in sealing relation to said open end thereof, said first and second rupturable walls being secured to each other.

* * * * *